United States Patent [19]

Cure et al.

[11] Patent Number: 4,964,736
[45] Date of Patent: Oct. 23, 1990

[54] IMMERSION MEASURING PROBE FOR USE IN MOLTEN METALS

[75] Inventors: Omer Cure, Diepenbeek; Theo P. C. Bollen, Genk, both of Belgium

[73] Assignee: Electro-Nite Co., Philadelphia, Pa.

[21] Appl. No.: 331,091

[22] Filed: Mar. 27, 1989

Related U.S. Application Data

[63] Continuation of Ser. No. 780,707, Sep. 26, 1985, abandoned, which is a continuation of Ser. No. 513,532, Jul. 13, 1983, abandoned.

[30] Foreign Application Priority Data

Oct. 8, 1982 [BE] Belgium .................................. 59866

[51] Int. Cl.$^5$ .............................................. G01K 1/12
[52] U.S. Cl. .................................... 374/140; 374/139; 374/140; 136/234
[58] Field of Search ............... 374/139, 140, 157, 142; 136/230, 232, 234; 204/422, 423, 210

[56] References Cited

U.S. PATENT DOCUMENTS

| | | | |
|---|---|---|---|
| 3,106,493 | 10/1963 | Japka | 136/234 |
| 3,288,654 | 11/1966 | Perrin et al. | 374/140 |
| 3,306,783 | 2/1967 | Silver | 136/234 |
| 3,353,808 | 11/1967 | Norburn | 374/140 |
| 3,379,578 | 4/1968 | Mctaggart et al. | 136/234 |
| 3,610,045 | 10/1971 | Shearman | 374/139 |
| 3,616,407 | 10/1971 | Engell et al. | 204/423 |
| 3,643,509 | 2/1972 | Surinx | 374/140 |
| 3,657,094 | 4/1972 | Hans et al. | 204/422 |
| 3,784,459 | 1/1974 | Jackson | 204/423 |
| 3,785,947 | 1/1974 | Baldwin et al. | 136/234 |
| 3,791,209 | 2/1974 | Norburn | 374/140 |
| 4,342,633 | 8/1982 | Cure | 204/423 |
| 4,401,389 | 8/1983 | Theuwis | 374/140 |

FOREIGN PATENT DOCUMENTS

| | | | |
|---|---|---|---|
| 1928845 | 5/1970 | Fed. Rep. of Germany . | |
| 1953580 | 11/1970 | Fed. Rep. of Germany | 204/422 |
| 2207307 | 8/1973 | Fed. Rep. of Germany | 374/140 |
| 144620 | 4/1962 | U.S.S.R. . | |
| 842107 | 4/1978 | U.S.S.R. . | |
| 1094180 | 12/1967 | United Kingdom . | |

Primary Examiner—William A. Cuchlinski, Jr.
Assistant Examiner—Patrick R. Scanlon
Attorney, Agent, or Firm—Panitch Schwarze Jacobs & Nadel

[57] ABSTRACT

An immersion probe as a preassembled unit includes a measuring head having a measuring element protected for minimizing trapping of gases by a sheath. The sheath is tapered toward a free end. The probe is adapted to be immersed in molten metal for measuring temperature and/or oxygen content.

7 Claims, 1 Drawing Sheet

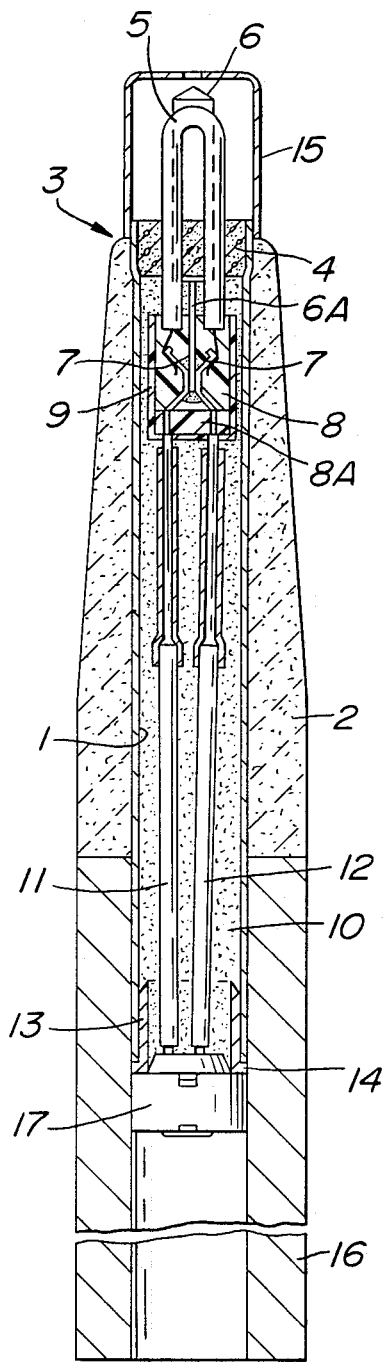

IMMERSION MEASURING PROBE FOR USE IN MOLTEN METALS

This application is a continuation of application Ser. No. 780,707, filed Sept. 26, 1985 and now abandoned, which was a continuation of application Ser. No. 513,532, filed July 13, 1983 and now abandoned.

FIELD OF THE INVENTION

The present invention is directed to an immersion measuring probe for measuring a characteristic of molten metal such as temperature and/or oxygen content.

BACKGROUND

Immersion measuring probes of the general type involved herein are disclosed in a number of prior art patents. For example, see Belgian patent Nos. 828,572; 881,886; 884,405; and 889,276. The prior art patents are generally characterized by a measuring head supported at one end of a paperboard tube. The paperboard tube is provided for its insulating protection when the probe is immersed into molten metal.

An oxygen probe supported by a quartz sheath of uniform wall thickness is taught by British Patent No. 1,094,180. A protective sheath of quartz is objectionable since quartz is transparent to thermal radiation. An oxygen probe supported by a quartz tube partially protected by a tapered graphite sleeve is taught by German Patent No. 1,928,845. The use of graphite as a protective sleeve is objectionable since it combines with oxygen with the result that the graphite sleeve burns off.

It has been found that the prior art probes of the type involved herein are inaccurate due to several features relating to the manner in which said prior art probes are constructed. A large number of solutions involving changes of material as well as changes in construction were investigated. In order to make a satisfactory probe which will give uniform accurate results, it was ascertained that the probe must meet the following criteria:

(a) A considerable reduction of the mass in the vicinity of the measuring was needed to diminish the cooling effect on the metal and thus enable more accurate measurements to be made quicker and at lower temperatures;

(b) When the probe includes a thermocouple, the temperature difference between its cold joints during immersion and temperature meaurement should be reduced;

(c) When the probe includes an oxygen sensor, it should be a solid electro-chemical cell and means should be provided to minimize the influence of oxygen liberated from the oxygen sensor so as to prevent liberated oxygen and other gases from being trapped adjacent to the sensor and thereby giving erroneous readings.

The probe of the present invention is directed to a solution of said problems.

SUMMARY OF THE INVENTION

The present invention is directed to an immersion probe which comprises unit including a support tube which defines the outer periphery of the unit. One end of the tube is an immersion end. At least one measuring element is supported on a measuring head which closes said tube adjacent its immersion end. A connector closes the other end of said tube. Electrical conductors in said tube extend from said connector to said measuring element. Heat insulating material is provided in said tube for protecting said conductors.

A means is provided on the tube for protecting the tube and for minimizing the ability of gasses to be trapped adjacent said measuring element. The means includes a heat insulating refractory sheath telescoped over a major portion of said tube beginning at the immersion of said tube. The sheath tapers toward the immersion end of the tube with the minimum wall thickness of the sheath being at said immersion end. The tube has an electrical conductive portion projecting beyond the sheath for contact with a bath of molten metal and is electrically coupled to said connector. An elongated hollow support is telescopically coupled to the other end of the tube for supporting the tube and the sheath during immersion into a bath of molten metal.

For the purpose of illustrating the invention, there is shown in the drawing, a form which is presently preferred; it being understood, however, that this invention is not limited to the precise arrangements and instrumentalities shown.

The drawing illustrates a longitudinal sectional view of the probe.

DETAILED DESCRIPTION

The measuring probe includes a preassembled unit with the outer periphery of such unit being defined by a cylindrical tube 1. The tube 1 is preferably a metal tube made from a material such as low carbon steel. The immersion end 3 of the probe is sealed by a plug of refractory heat resistant material such as cement. Plug 4 constitutes a measuring head for supporting one or more measuring elements. As illustrated, the measuring head supports the thermocouple 5 partially disposed within the quartz tube coated with aluminum oxide and a solid electrolite electro-chemical oxygen sensing cell 6, a portion of which extends into the tube beyond the plug 4 opposite the emerging end.

The cold joints 7 of the thermocouple 5 are embedded in a gas tight enclosure such as a body of silicone 8 surrounded by a small plastic casing 9. The conductors at the cold joints 7 are V-shaped with the apexes adjacent one another but electrically insulated from one another by the silicone 8. The bottom wall of the casing 9 may be separable and defined by a plastic disk 8A. The tube 1 is filled with a heat insulating material free from crystal water such as resin coated molding sand 10 packed loosely so as to be gas permeable and through which conductors 11 and 12 pass. Conductors 11 and 12 extend from the cold joints 7 to a connector 17. Connector 17 has an electrically conductive sleeve 13 in intimate contact with the electrically conductive tube 1. An electrical conductor 6A extends between the oxygen sensor 6 and one of the cold joints 7. Tube 1 acts as a conductor for closing the circuit of the cell 6.

A heat insulating refractory sheath 2 is telescoped over the major length of the tube 1 beginning at the immersion end 3. The sheath 2 is supported by the tube 1 and is bonded thereto in any convenient manner. Sheath 2 is tapered along a major portion of its length toward the immersion end 3 for protecting the tube 1 and for minimizing the ability of gasses to be trapped adjacent the measuring elements 5 and 6. Sheath 2 is preferably made from a refractory material such as resin coated molding sand. Sheath 2 could be made from other materials such as aluminum oxide or zirconium oxide but should not be made from quartz or graphite.

In order that the tube 1 may perform the additional function of completing the circuit for the oxygen sensor 6, it projects beyond the immersion end of the sheath 2 so that it may contact the molten bath after the protective cap 15 is consumed by the bath as the probe is inserted through a layer of slag. To facilitate immersing the probe into molten metal, a support is provided in the form of a paperboard tube 16 which is force-fit over the tube 1. Adjacent ends of the sheath 2 and support 16 are in contact with one another.

The preferred dimensions for the sheath 2 are by way of example: a length of 10 centimeters, an external diameter of 2.5 centimeters at the immersion end 3, maximum external diameter of 3.7 to 4.8 centimeters; and an internal diameter of about 1.8 centimeters.

In addition to increased accuracy, the probe of the present invention has other advantages: small mass of materials in the vicinity of the measuring elements, excellent protection of the cold joints against mutual temperature differences, a favorable shape for causing the probe to penetrate the bath, etc. Other advantages include the ability to preassemble the probe on a production line basis. In this regard, the electrically conductive tube 1 performs the dual function of providing support for elements therewithin which may be preassembled as a unit and then joined to the sheath 2 and support 16 in an economical manner requiring little or no skill on the part of the workers.

The present invention may be embodied in other specific forms without departing from the spirit or essential attributes thereof and, accordingly, reference should be made to the appended claims, rather than to the foregoing specifications, as indicating the scope of the invention.

I claim:

1. An immersion measuring probe for measurements in a molten metal bath comprising:
    an elongated hollow electrically conductive tube, said tube having an immersion end and a connector end;
    a measuring head closing the internal portion of said immersion end of said tube, said measuring head having
    a non-conductive support plug,
    a thermocouple element supported by said plug and having one end projecting from said immersion end of said tube and an electrically conductive portion extending into said tube beyond said plug,
    an electro-chemical cell extending through said plug having one end adjacent to said projecting end of the thermocouple element and an electronically conductive portion extending into said tube beyond said plug;
    a gas impermeable enclosure receiving the electrically conductive portions of said thermocouple and said cell, said enclosure being closely adjacent to said measuring head within said tube;
    electrical conductors extending from said enclosure to said connector end of said tube;
    an electrical connector closing said connector end of said tube and providing electrical connections for said thermocouple, said cell and said tube;
    said tube between said plug and said connector being filled with a heat insulating particulate material which is loosely packed such that it is gas permeable;
    a sheathing surrounding a major portion of the length of said tube, said sheathing being made of a fireproof, refractory heat resistant material attached to the exterior of said tube, the outer surface of said sheathing being tapered towards the immersion end of said tube such that a minimum thickness of said sheathing is directly adjacent to and exposing said immersion end of said tube for minimizing trapped gases adjacent the measuring head when immersed into the metal bath, the opposite end of said sheathing from said tapered end forming a shoulder adjacent to said connector end of said tube; and
    an elongated hollow support for receiving said shoulder of said sheathing in an abutting relationship such that the end of said tube is inserted into said support and said outer diameter of said sheathing and said support are substantially the same at said shoulder.

2. An immersion measuring probe as claimed in claim 1 wherin said thermocouple element further comprises a quartz tube having an aluminum oxide coating thereon.

3. An immersion measuring probe for measurements in a molten metal bath comprising:
    an elongated hollow electrically conductive tube, said tube having an immersion end and a connector end;
    a measuring head closing the internal portion of said immersion end of said tube, said measuring head having
    a non-conductive support plug,
    a thermocouple element supported by said plug and having one end projecting from said immersion end of said tube and an electrically conductive portion extending into said tube beyond said plug,
    a gas impermeable enclosure receiving the electrically conductive portions of said thermocouple, said enclosure being closely adjacent to said measuring head within said tube;
    electrical conductors extending from said enclosure to said connector end of said tube;
    an electrical connector closing said connector end of said tube and providing an electrical connection for said thermocouple;
    said tube between said plug and said connector being filled with a heat insulating particulate material which is loosely packed such that it is gas permeable;
    a sheathing surrounding a major portion of the length of said tube, said sheathing being made of a fireproof, refractory heat resistant material attached to said tube exterior, the outer surface of said sheathing being tapered towards the immersion end of said tube such that a minimum thickness of said sheathing is directly adjacent to and exposing said immersion end of said tube for minimizing trapped gases adjacent to the measuring head when immersed in a metal bath, the opposite end of said sheathing from said tapered end forming a shoulder adjacent to said connector end of said tube; and
    an elongated hollow support for receiving said shoulder of said sheathing in an abutting relationship such that the end of said tube is inserted into said support and said outer diameter of said sheathing and said support are substantially the same at said shoulder.

4. An immersion probe for measurements in a molten metal bath comprising:

an elongated hollow electrically conductive tube, said tube having an immersion end and a connector end;

a measuring head closing the internal portion of said immersion end of said tube, said measuring head having a non-conductive support plug, an electro-chemical cell extending through said plug having one end projecting form said immersion end of said tube and its opposite extending into said tube beyond said plug;

a gas impermeable enclosure receiving the electrically conductive portion of said cell, said enclosure being closely adjacent to said measuring head within said tube;

electrical conductors extending from said enclosure to said connector end of said tube;

an electrical connector closing said connector end of said tube and providing electrical connections for said cell and said tube;

said tube between said plug and said connector being filled with a heat insulating particulate material which is loosely packed such that it is gas permeable;

a sheathing surrounding a major portion of the length of said tube, said sheathing being made of a fireproof, refractory heat resistant material attached to said tube exterior, the outer surface of said sheathing being tapered towards the immersion end of said tube such that a minimum thickness of said sheathing is directly adjacent to and exposing said immersion end of said tube for minimizing trapped gases adjacent to the measuring head when immersed into a metal bath, the opposite end of said sheathing from said tapered end forming a shoulder adjacent to said connector end of said tube; and an elongated hollow support for receiving said shoulder of said sheathing in an abutting relationship such that the end of said tube is inserted into said support and said outer diameter of said sheathing and said support are substantially the same at said shoulder.

5. An immersion measuring probe for measurements in a molten metal bath comprising:

an elongated hollow electrically conductive tube, said tube having an immersion end and a connector end;

a measuring head closing the internal portion of said immersion end of said tube, said measuring head having a non-conductive support plug, a thermocouple element supported by said plug and having one end projecting from said immersion end of said tube and an electrically conductive portion extending into said tube beyond said plug, an electrochemical cell extending through said plug having one end projecting from the immersion end of said tube adjacent to said projecting end of the thermocouple element and an electrically conducting portion extending into said tube beyond said plug;

means within said tube for receiving the electrically conductive portions of said thermocouple and said cell;

electrical conductors extending from said receiving means to said connector end of said tube;

an electrical connector closing said connector end of said tube and providing electrical connections for said thermocouple, said cell and said tube;

said tube between said plug and said connector being filled with a heat insulating particulate material which is loosely packed such that it is gas permeable;

a sheathing surrounding a major portion of the length of said tube, said sheathing being made of a fireproof, refractory heat resistant material attached to the exterior of said tube, the outer surface of said sheathing being tapered towards the immersion end of said tube such that a minimum thickness of said sheathing is directly adjacent to and exposing said immersion end of said tube for minimizing trapped gases adjacent the measuring head when immersed into the metal bath, the opposite end of said sheathing from said tapered end forming a shoulder adjacent to said connector end of said tube; and an elongated hollow support for receiving said shoulder of said sheathing in an abutting relationship such that the end of said tube is inserted into said support and said outer diameter of said sheathing and said support are substantially the same at said shoulder.

6. An immersion measuring probe for measurements in a molten metal bath comprising:

an elongated hollow electrically conductive tube, said tube having an immersion end and a connector end;

a measuring head closing the internal portion of said immersion end of said tube, said measuring head having a non-conductive support plug, a thermocouple element supported by said plug and having one end projecting from said immersion end of said tube and having an electrically conductive portion extending into said tube beyond said plug, means within said tube for receiving the electrically conductive portion of said thermocouple;

electrical conductors extending from said receiving means to said connector end of said tube;

an electrical connector closing said connector end of said tube and providing an electrical connection for said thermocouple;

said tube between said plug and said connector being filled with a heat insulating particulate material which is loosely packed such that it is gas permeable;

sheathing surrounding a major portion of the length of said tube, said sheathing being made of a fireproof, refractory heat resistant material attached to said tube exterior, the outer surface of said sheathing being tapered towards the immersion end of said tube such that a minimum thickness of said sheathing is directly adjacent to and exposing said immersion end of said tube for minimizing trapped gases adjacent to the measuring head when immersed in a metal bath, the opposite end of said sheathing form said tapered end forming a shoulder adjacent to said connector end of said tube; and an elongated hollow support for receiving said shoulder of said sheathing in an abutting relationship such that the end of said tube is inserted into said support and said outer diameter of said sheathing and said support are substantially the same at said shoulder.

7. An immersion probe for measurements in a molten metal bath comprising:
   an elongated hollow electrically conductive tube, said tube having an immersion end and a connector end;
   a measuring head closing the internal portion of said immersion end of said tube, said measuring head having
   a non-conductive support plug,
   an electrochemical cell extending through said plug having one end projecting form said immersion end of said tube and an electrically conductive portion extending into said tube beyond said plug;
   means within said tube for receiving the electrically conductive portion of said cell;
   electrical conductors extending from said receiving means to said connector end of said tube;
   an electrical connector closing said connector end of said tube and providing electrical connections for said cell and said tube;
   said tube between said plug and said connector being filled with a heat insulating particulate material which is loosely packed such that it is gas permeable;
   sheathing surrounding a major portion of the length of said tube, said sheathing being made of a fireproof, refractory heat resistant material attached to said tube exterior, the outer surface of said sheathing being tapered towards the immersion end of said tube such that a minimum thickness of said sheathing is directly adjacent to and exposing said immersion end of said tube for minimizing trapped gases adjacent to the measuring head when immersed into a metal bath, the opposite end of said sheathing from said tapered end forming a shoulder adjacent to said connector end of said tube; and
   an elongated hollow support for receiving said shoulder of said sheathing in an abutting relationship such that the end of said tube is inserted into said support and said outer diameter of said sheathing and said support are substantially the same at said shoulder.

* * * * *

(12) EX PARTE REEXAMINATION CERTIFICATE (5121st)
United States Patent
Cure et al.

(10) Number: US 4,964,736 C1
(45) Certificate Issued: Jun. 14, 2005

(54) IMMERSION MEASURING PROBE FOR USE IN MOLTEN METALS

(75) Inventors: Omer Cure, Diepenbeek (BE); Theo P. C. Bollen, Genk (BE)

(73) Assignee: Heraeus Electro-Nite Co.

Reexamination Request:
No. 90/006,904, Jan. 12, 2004

Reexamination Certificate for:
Patent No.: 4,964,736
Issued: Oct. 23, 1990
Appl. No.: 07/331,091
Filed: Mar. 27, 1989

Related U.S. Application Data

(63) Continuation of application No. 06/780,707, filed on Sep. 26, 1985, now abandoned, which is a continuation of application No. 06/513,532, filed on Jul. 13, 1983, now abandoned.

(30) Foreign Application Priority Data

Oct. 8, 1982 (BE) .................................................. 59866

(51) Int. Cl.[7] .................................................. G01K 1/12

(52) U.S. Cl. .................. 374/140; 374/139; 136/234
(58) Field of Search ................................ 374/140, 139, 374/157, 142; 136/230, 232, 234; 204/422, 423, 210

(56) References Cited

U.S. PATENT DOCUMENTS 3,784,459 A     1/1974   Jackson
3,844,172 A   * 10/1974   Jeric ........................... 136/230

FOREIGN PATENT DOCUMENTS

DE           2207307       8/1973
JP            50000/1977     11/1978
JP            148119/1979     6/1981

* cited by examiner

Primary Examiner—Diego F. F. Gutierrez

(57) ABSTRACT

An immersion probe as a preassembled unit includes a measuring head having a measuring element protected for minimizing trapping of gases by a sheath. The sheath is tapered toward a free end. The probe is adapted to be immersed in molten metal for measuring temperature and/or oxygen content.

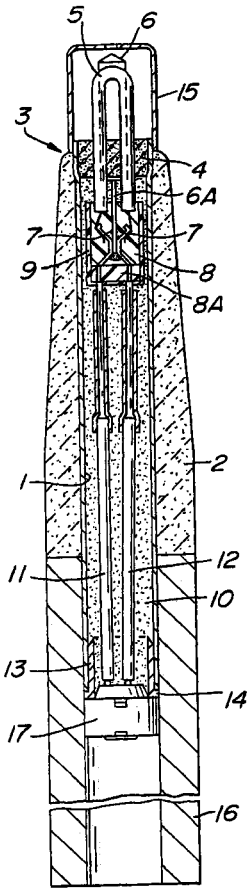

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *